US012016556B2

(12) United States Patent
Evans et al.

(10) Patent No.: US 12,016,556 B2
(45) Date of Patent: Jun. 25, 2024

(54) HANDHELD ELECTROMECHANICAL SURGICAL SYSTEM

(71) Applicant: Covidien LP, Mansfield, MA (US)

(72) Inventors: Christopher K. Evans, Southington, CT (US); Robert H. Knapp, Middlebury, CT (US)

(73) Assignee: Covidien LP, Mansfield, MA (US)

( * ) Notice: Subject to any disclaimer, the term of this patent is extended or adjusted under 35 U.S.C. 154(b) by 73 days.

(21) Appl. No.: 17/246,828

(22) Filed: May 3, 2021

(65) Prior Publication Data

US 2022/0346777 A1 Nov. 3, 2022

(51) Int. Cl.
*A61B 17/072* (2006.01)
*A61B 17/068* (2006.01)
*A61B 90/00* (2016.01)

(52) U.S. Cl.
CPC ........ *A61B 17/0686* (2013.01); *A61B 17/072* (2013.01); *A61B 90/06* (2016.02); *A61B 2017/07257* (2013.01); *A61B 2017/07271* (2013.01); *A61B 2017/07278* (2013.01);
(Continued)

(58) Field of Classification Search
CPC ...... A61B 90/06; A61B 17/068; A61B 17/072
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| 3,273,562 A | 9/1966 | Brown |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

The International Search Report and Written Opinion dated Aug. 3, 2022 issued in corresponding PCT Appln. No. PCT/IB2022/053862.

(Continued)

*Primary Examiner* — Gloria R Weeks

(74) *Attorney, Agent, or Firm* — Carter, DeLuca & Farrell LLP

(57) ABSTRACT

A surgical device includes an end effector having a pair of opposing jaw members and a drive beam movable longitudinally through the pair of opposing jaw members thereby approximating the pair of opposing jaw members relative to each other. The device also includes an adapter assembly configured to selectively couple to the end effector. The adapter assembly includes an actuation assembly configured to mechanically engage the drive beam and to move the drive beam longitudinally. The device also includes a handle assembly configured to selectively couple to the adapter assembly. The handle assembly includes: a power source, a motor coupled to the power source, a sensor configured to measure a force imparted on the drive beam, and a motor controller configured to control the motor to maintain constant force on the drive beam based on the force measured by the sensor during longitudinal movement of the drive beam approximating the pair of opposing jaw members closer relative to each other.

17 Claims, 10 Drawing Sheets

(52) U.S. Cl.
CPC ............... *A61B 2017/07285* (2013.01); *A61B 2090/064* (2016.02)

(56) References Cited

U.S. PATENT DOCUMENTS

| | | |
|---|---|---|
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |

(56) References Cited

U.S. PATENT DOCUMENTS

| | | |
|---|---|---|
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |

(56) References Cited

U.S. PATENT DOCUMENTS

| | | | |
|---|---|---|---|
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1* | 9/2008 | Marczyk ............ A61B 17/07207 |
| | | | 227/176.1 |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,276,801 B2* | 10/2012 | Zemlok ............... A61B 90/90 |
| | | | 227/176.1 |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,237,921 B2* | 1/2016 | Messerly ....... A61B 17/320068 |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 9,743,929 B2* | 8/2017 | Leimbach ................ B25F 5/00 |
| 10,201,365 B2* | 2/2019 | Boudreaux ............ A61B 90/06 |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2006/0273135 A1* | 12/2006 | Beetel ................. A61B 17/128 |
| | | | 227/175.1 |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |

(56) References Cited

U.S. PATENT DOCUMENTS

| | | |
|---|---|---|
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0270355 A1* | 10/2010 | Whitman .............. A61B 17/072 227/176.1 |
| 2010/0312257 A1 | 12/2010 | Aranyi |
| 2010/0320254 A1 | 12/2010 | Zemlok et al. |
| 2011/0034910 A2 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0204119 A1* | 8/2011 | McCuen .............. A61B 17/068 227/175.1 |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2015/0280384 A1* | 10/2015 | Leimbach ................. A61L 2/07 227/175.1 |
| 2019/0099180 A1* | 4/2019 | Leimbach ............ A61B 17/072 |
| 2019/0200977 A1* | 7/2019 | Shelton, IV ......... A61B 17/068 |
| 2019/0314015 A1* | 10/2019 | Shelton, IV ......... A61B 17/072 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |
| WO | 2018234893 A1 | 12/2018 |
| WO | 2019003023 A1 | 1/2019 |

OTHER PUBLICATIONS

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM" ; IC-ON-LINE, Electronic Component Manufacturers, pp. 1-2; Aug. 2013.

* cited by examiner

HANDHELD ELECTROMECHANICAL SURGICAL SYSTEM

BACKGROUND

1. Technical Field

The present disclosure relates to surgical devices. More specifically, the present disclosure relates to handheld electromechanical surgical systems for performing surgical procedures.

2. Background of Related Art

Surgical fastener devices for applying fasteners or staples to tissue are well known. These fastener devices include single-use devices which are preloaded with one or more staples and are disposable after a single use. Multiple use devices are also available and are preloaded with a plurality of staples. Multiple use devices may include a handle assembly that is electromechanically, e.g., powered, or manually actuated. These devices may be used with single use loading units (SULU) or multiple use loading units (MULU). The loading units include a body and an end effector, and are attached to the handle assembly, either directly or via an adapter assembly couplable to the handle assembly. The loading units may also include an articulating end effector. In powered surgical devices, which utilize motors to actuate and/or articulate the end effector, the motors may result in slower ejection of staples than manually actuated surgical devices. Thus, there is a need for powered surgical staplers configured to eject staplers at a faster rate commensurate with manual staplers.

SUMMARY

According to one embodiment of the present disclosure, a surgical device is disclosed. The surgical device includes an end effector having a pair of opposing jaw members and a drive beam movable longitudinally through the pair of opposing jaw members thereby approximating the pair of opposing jaw members relative to each other. The device also includes an adapter assembly configured to selectively couple to the end effector. The adapter assembly includes an actuation assembly configured to mechanically engage the drive beam and to move the drive beam longitudinally. The device also includes a handle assembly configured to selectively couple to the adapter assembly. The handle assembly includes: a power source, a motor coupled to the power source, a sensor configured to measure a force imparted on the drive beam, and a motor controller configured to control the motor to maintain constant force on the drive beam based on the force measured by the sensor during longitudinal movement of the drive beam approximating the pair of opposing jaw members closer relative to each other.

Implementations may include one or more of the following features. According to one aspect of the above embodiment, one jaw member of the pair of opposing jaw members may include a plurality of staples. The end effector may further include an actuation sled movable through the one jaw member of the pair of opposing jaw members to eject the plurality of staples. The drive beam may be configured to engage the actuation sled to move the actuation sled through the one jaw member of the pair of opposing jaw members. The drive beam may further include a distally facing knife. The motor controller includes a proportional-integral-derivative (PID) controller configured to receive the measured force as input and to output motor control signals to maintain the constant force on the drive beam. The motor control signals may be pulse-width-modulated. The motor controller may be further configured to ramp up to the constant force at a constant rate. The handle assembly may further include a user input button and a main controller configured to receive an input signal from the user input button and to signal the motor controller to control the motor.

According to another embodiment of the present disclosure, a surgical device is disclosed. The surgical device includes an end effector having an anvil assembly, a cartridge assembly having a plurality of staples, and a drive beam movable longitudinally through the anvil assembly and the cartridge assembly thereby approximating the anvil assembly and the cartridge assembly relative to each other and ejecting the plurality of staples. The surgical device also includes an adapter assembly configured to selectively couple to the end effector. The adapter assembly includes an actuation assembly configured to mechanically engage the drive beam and to move the drive beam longitudinally. The surgical device also includes a handle assembly configured to selectively couple to the adapter assembly. The handle assembly includes: a power source, a motor coupled to the power source, a sensor configured to measure a force imparted on the drive beam, and a motor controller configured to control the motor to maintain constant force on the drive beam based on the force measured by the sensor during movement of the drive beam to approximate the anvil assembly and the cartridge assembly relative to each other and eject the plurality of staples.

Implementations may include one or more of the following features. According to one aspect of the above embodiment, the end effector may include an actuation sled movable through the cartridge assembly and configured to eject the plurality of staples. The drive beam may be configured to engage the actuation sled to move the actuation sled through the cartridge assembly. The drive beam may further include a distally facing knife. The motor controller may include a proportional-integral-derivative (PID) controller configured to receive the measured force as input and to output motor control signals to maintain the constant force on the drive beam. The motor control signals may be pulse-width-modulated. The motor controller may be further configured to ramp up to the constant force at a constant rate.

According to a further embodiment of the present disclosure, a method for controlling a surgical device is disclosed. The method includes activating a motor coupled to a drive beam configured to move longitudinally through an anvil assembly and a cartridge assembly of an end effector. The method also includes approximating the anvil assembly and the cartridge assembly closer relative to each other. The method also includes ejecting a plurality of staples disposed in the cartridge assembly. The method further includes measuring a force imparted on the drive beam. The method further includes controlling the force imparted on the drive beam to remain constant at a setpoint during longitudinal movement.

Implementations may include one or more of the following features. According to one aspect of the above embodiment, the method may also include ramping up the force imparted on the drive beam at a constant rate to reach the setpoint. The method may further include advancing a knife through the anvil assembly and the cartridge assembly. The method may also include controlling the force by processing the measured force as input through a proportional-integralderivative (PID) controller and outputting the motor control signals from the PID controller to maintain the constant force on the drive beam.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
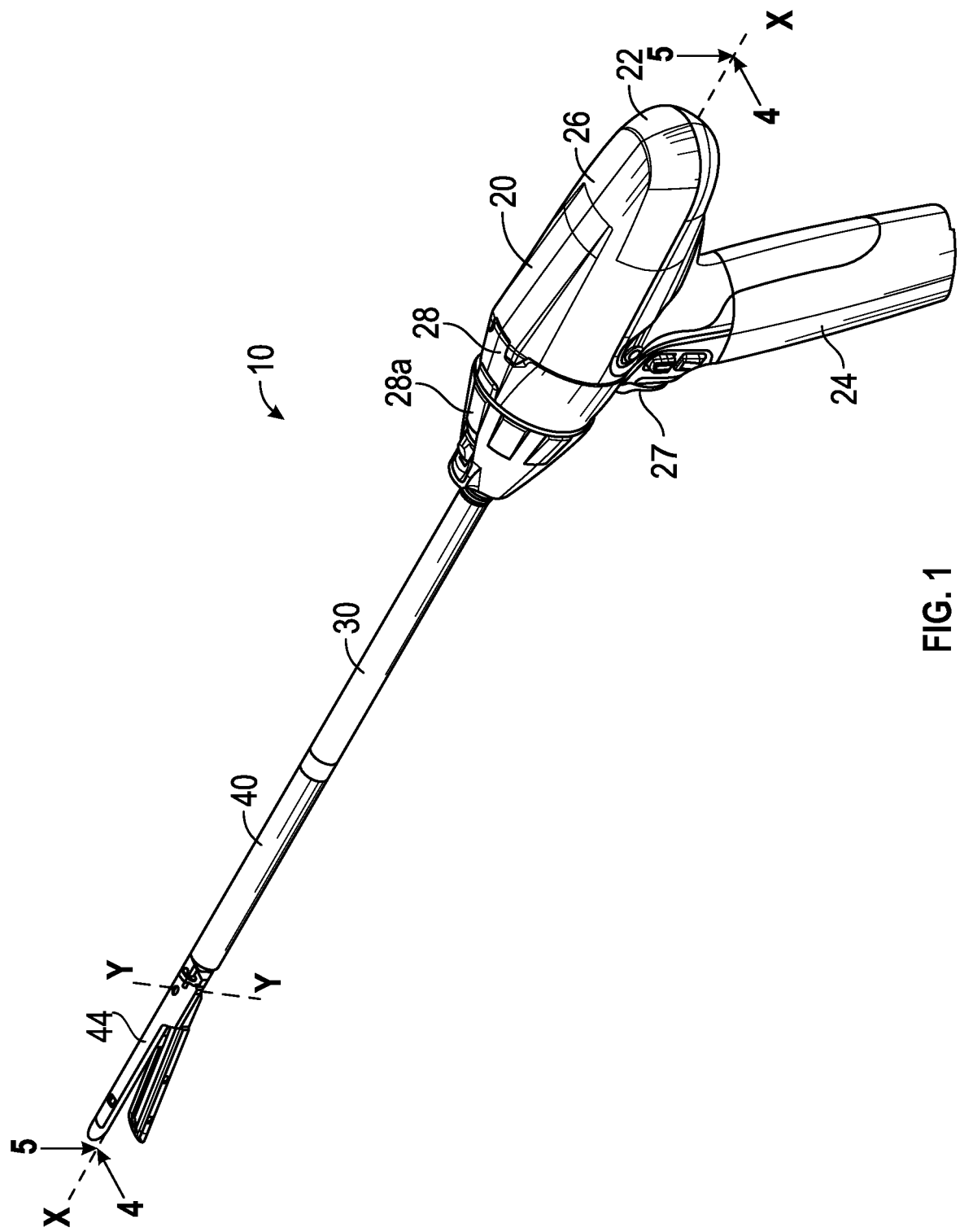
FIG. 1 is a perspective view of a handheld surgical device including a handle assembly, an adapter assembly, and a surgical loading unit according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered surgical device 10 (e.g., stapler) having a handle assembly, an adapter assembly coupled to the handle assembly, and an end effector coupled to the adapter assembly. With reference to FIG. 1, a powered surgical device 10 includes a handle assembly 20, which is configured for selective connection with an adapter assembly 30, which in turn, is configured for selective connection with a loading unit 40 having an end effector 44. Although generally referred to as being a powered surgical device, it is contemplated that the surgical device 10 may be manually actuated and may include various configurations.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. The handle assembly 20 also includes a plurality of controls 23, which may include buttons 27, touchscreen, or any other user input devices, for allowing the clinician to control the operation of the surgical device 10.

Figure 2:
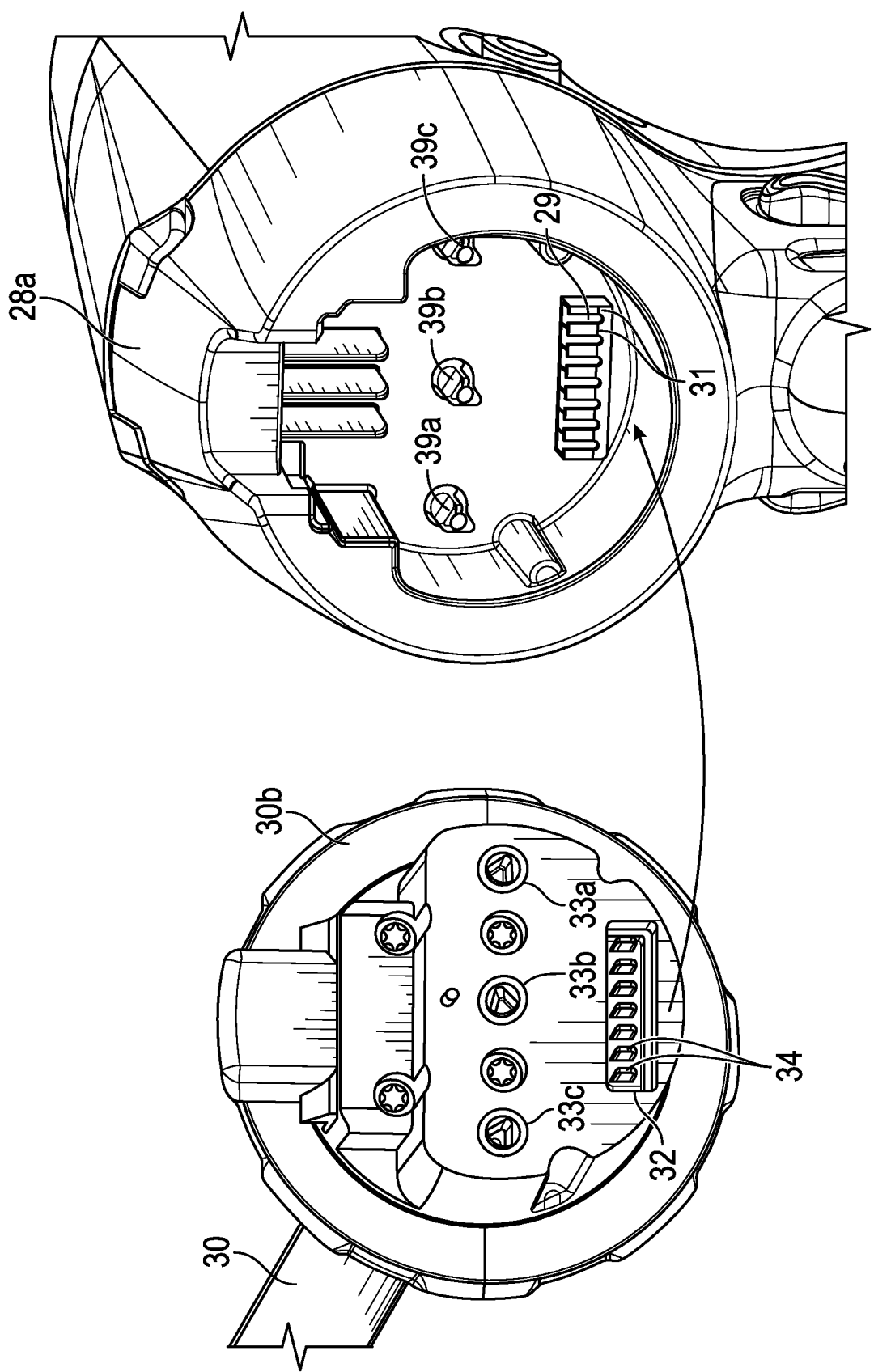
FIG. 2 is a perspective view illustrating a connection of the adapter assembly and the handle assembly of FIG. 1 according to an embodiment of the present disclosure.

As shown in FIG. 2, a distal portion of the upper housing portion 28 defines a nose or connecting portion 28a that is configured to accept a proximal end portion 30b of the adapter assembly 30. The connecting portion 28a of the upper housing portion 28 includes an electrical receptacle 29 having a plurality of electrical contacts 31, which are in electrical communication with electronic (e.g., a main controller circuit board 142 of FIG. 8) and electrical components (e.g., a rechargeable battery 144 of FIGS. 3 and 8) of the handle assembly 20. The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

Figure 3:
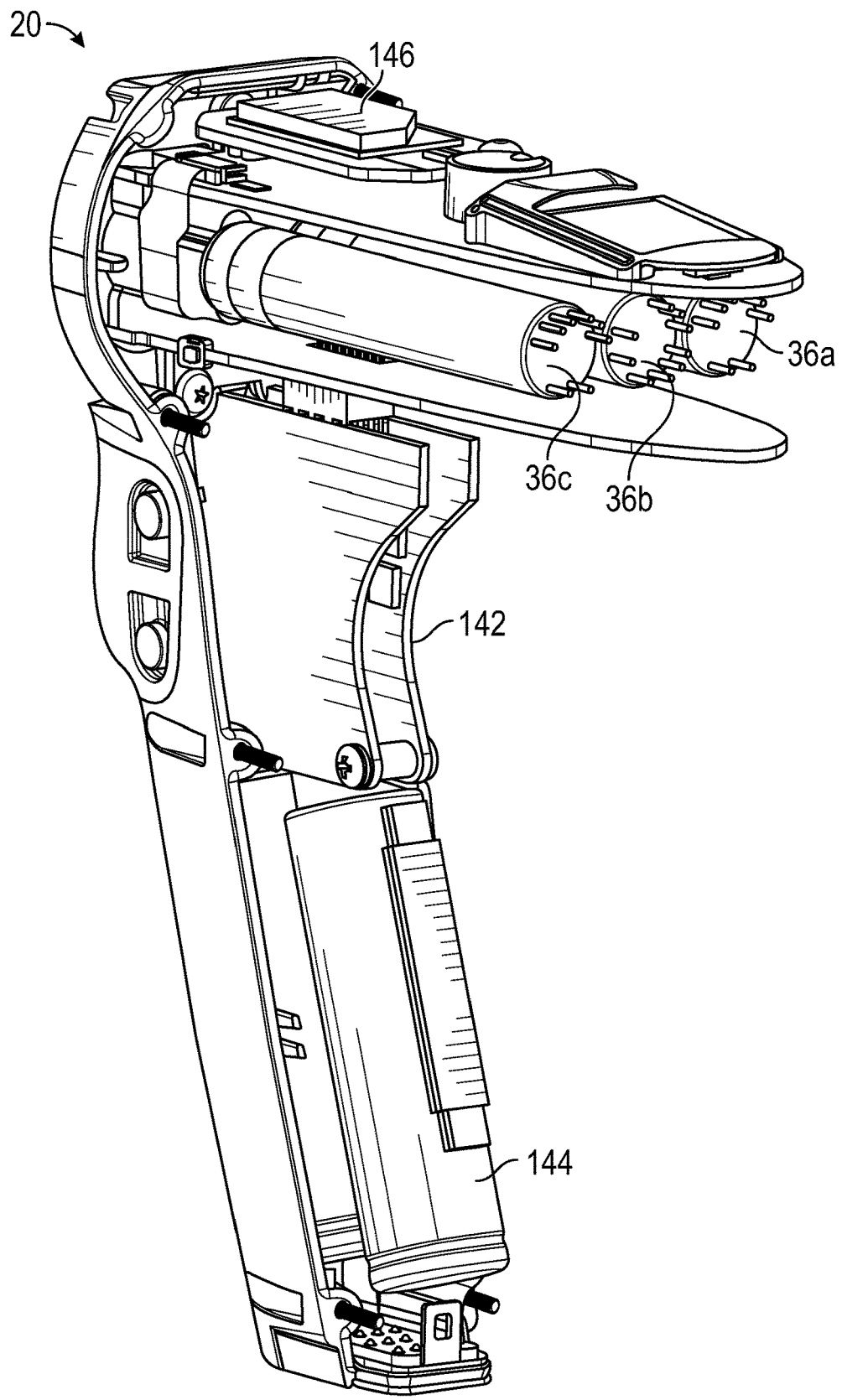
FIG. 3 is perspective view of internal components of the handle assembly according to an embodiment of the present disclosure.

With reference to FIG. 3, the handle assembly 20 includes motors 36a, 36b, 36c, which are coupled to corresponding drive shafts 39a, 39b, 39c (FIG. 2), which are configured to engage respective sockets 33a, 33b, 33c on the proximal end portion 30b, such that rotation of the drive shafts 39a, 39b, 39c is imparted on the sockets 33a, 33b, 33c.

Figure 4:
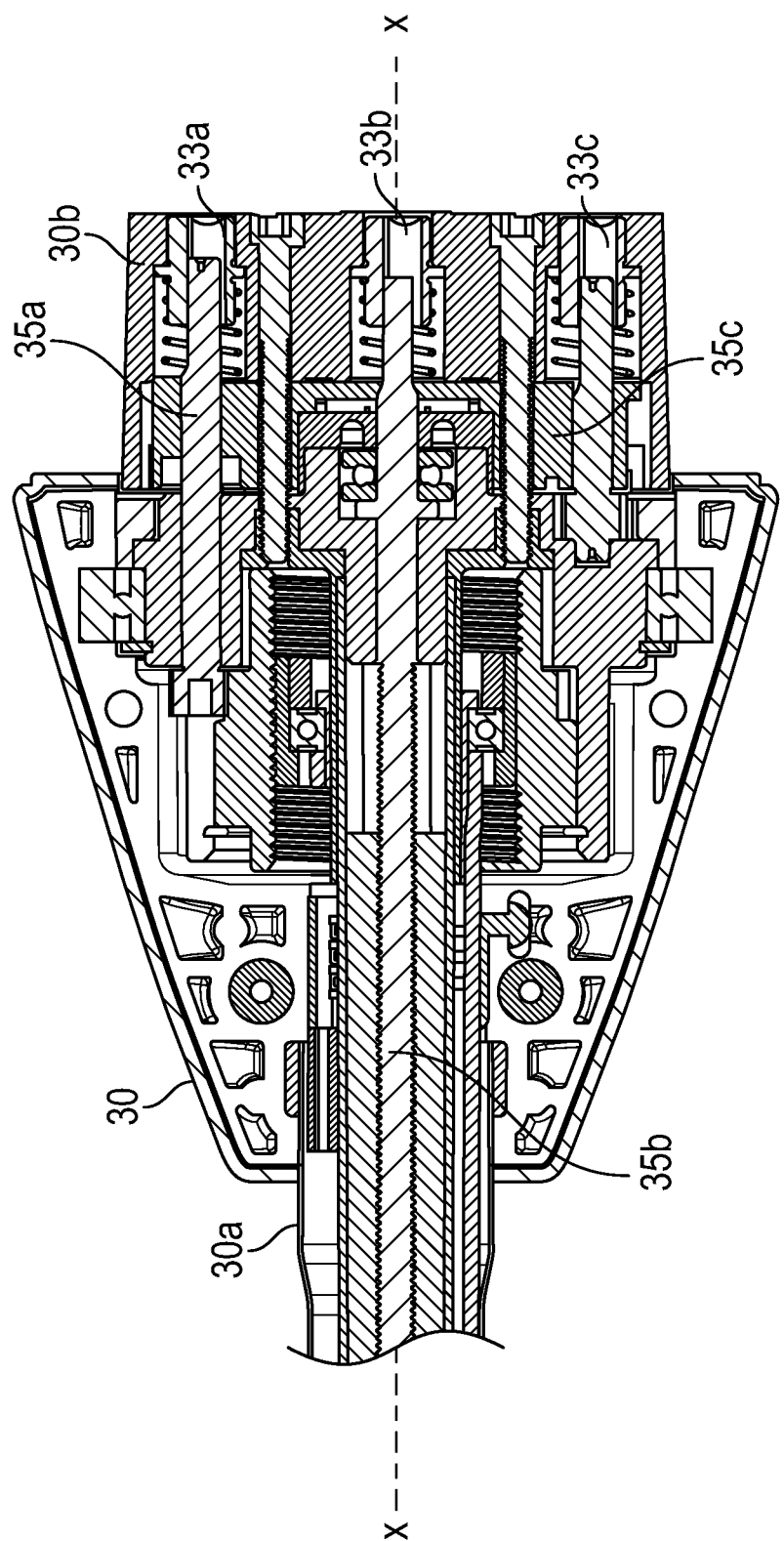
FIG. 4 is cross-sectional view of the adapter assembly taken along a section plane "4-4" of FIG. 1 according to an embodiment of the present disclosure.
Figure 5:
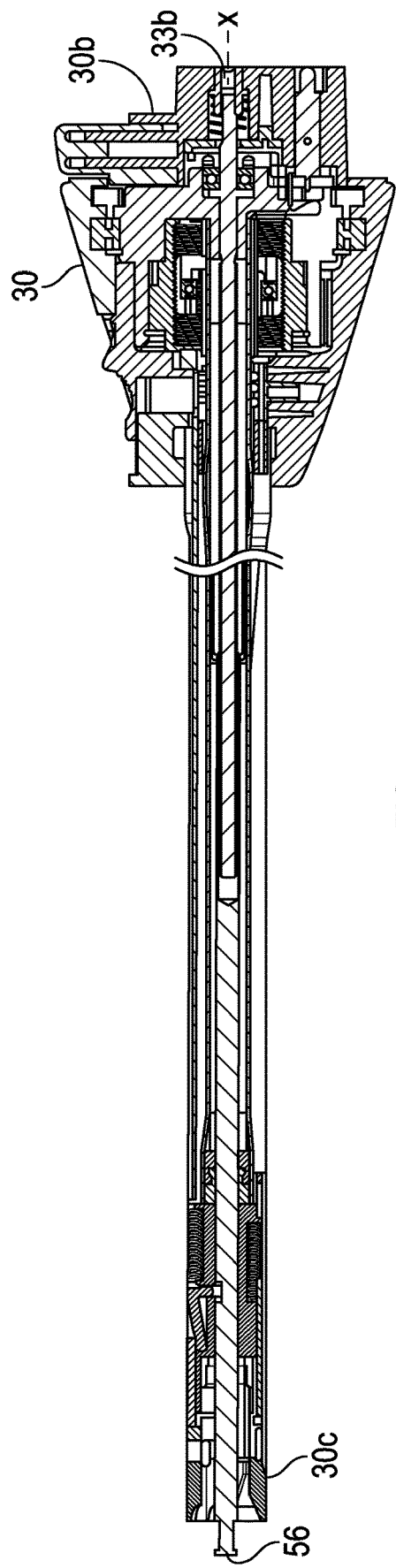
FIG. 5 is cross-sectional view of the adapter assembly taken along a section plane "5-5" of FIG. 1 according to an embodiment of the present disclosure.
Figure 6:
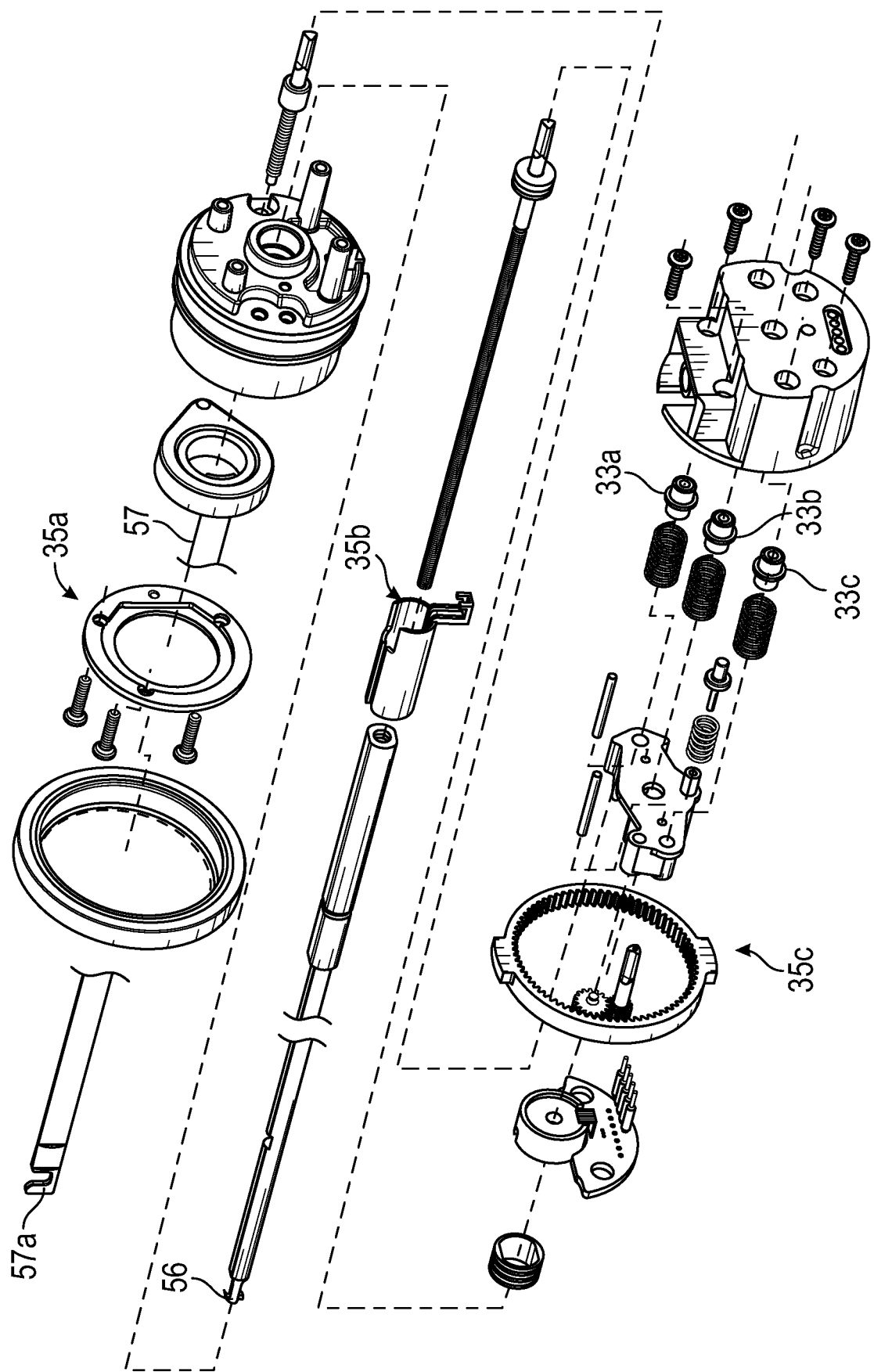
FIG. 6 is a perspective view, with parts separated, of the adapter assembly of FIG. 1 according to an embodiment of the present disclosure.

With reference to FIGS. 4-6, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the loading unit 40. The adapter assembly 30 includes actuation assemblies 35a, 35b, 35c each of which is coupled to one of the sockets 33a, 33b, 33c (FIG. 6). The actuation assemblies 35a, 35b, 35c are configured to transfer rotational motion of the sockets 33a, 33b, 33c into linear motion and/or rotational motion, such that the adapter assembly 30 is configured to convert a rotational motion provided by the handle assembly 20 into axial translation for rotating the adapter assembly 30 about a longitudinal axis X-X, articulate the loading unit 40, clamp tissue, eject fasteners, and cut fastened tissue.

With reference to FIG. 6, the actuation assembly 35a, actuated by the motor 36a, includes an articulation link 57 having a hook 57a disposed at a distal end portion of the articulation link 57. Longitudinal movement of the articulation link 57 is used to articulate the end effector 44 about an articulation axis Y-Y (FIGS. 1 and 7), which is perpendicular to the longitudinal axis X-X. The actuation assembly 35b, actuated by the motor 36b, includes a drive member 56, which is used to operate an anvil assembly 46 and a cartridge assembly 48 of the end effector 44. The actuation assembly 35c, actuated by the motor 36c, is used to rotate the adapter assembly 30 about the longitudinal axis X-X.

Figure 7:
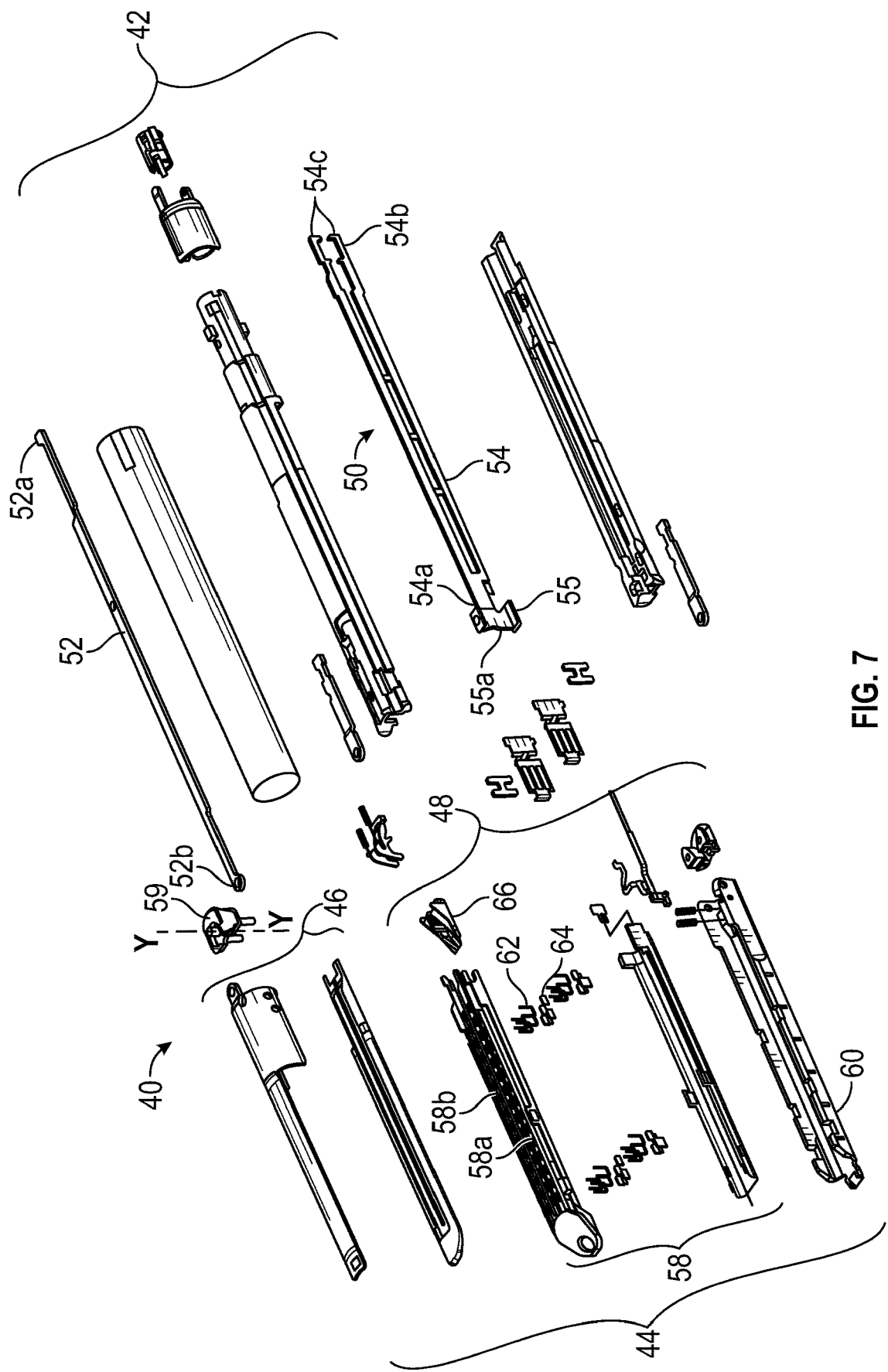
FIG. 7 is a perspective view, with parts separated, of the surgical loading unit of FIG. 1 according to an embodiment of the present disclosure.

With reference to FIGS. 1 and 7, an embodiment of the loading unit 40 is shown. The loading unit 40 includes a proximal body portion 42 and the end effector 44. Proximal body portion 42 is releasably attached to the distal end portion 30c of adapter assembly 30, and end effector 44 is pivotally attached to a distal end of proximal body portion 42. End effector 44 includes the anvil assembly 46 and the cartridge assembly 48. Anvil assembly 46 is pivotable in relation to the cartridge assembly 48 and is movable between an open or unclamped position and a closed or clamped position. Proximal body portion 42 includes a drive assembly 50 and an articulation link 52.

Drive assembly 50 includes a flexible drive beam 54 having a distal end portion 54a and a proximal engagement section 54b. The distal end portion 54a includes an I-beam 55 having a knife 55a. The I-beam 55 is configured to travel through the anvil assembly 46 and the cartridge assembly 48, thereby pushing the anvil assembly 46 toward the cartridge assembly 48 to clamp tissue. The proximal engagement section 54b includes diametrically opposed inwardly extending fingers 54c that engage the drive member 56 (FIGS. 5 and 6) to fixedly secure drive member 56 to the proximal end of flexible drive beam 54. Drive member 56 is actuated by the actuation assembly 35b of adapter assembly 30.

Cartridge assembly 48 of end effector 44 includes a staple cartridge 58 removably supported in a carrier 60. Staple cartridge 58 defines a central longitudinal slot 58a, and a plurality of linear rows of staple retention slots 58b positioned on each side of the central longitudinal slot 58a. Each of the staple retention slots 58b receives a staple 62 and a portion of a staple pusher 64. During operation of the surgical device 10, drive assembly 50 abuts an actuation sled 66 and pushes actuation sled 66 through the staple cartridge 58. As the actuation sled 66 moves through staple cartridge 58, cam wedges of the actuation sled 66 sequentially engage staple pushers 64 to move staple pushers 64 vertically within staple retention slots 58b and sequentially eject the staples 62 therefrom for formation against an anvil plate 46a of anvil assembly 46.

Proximal body portion 42 of loading unit 40 includes an articulation link 52 having a hooked proximal end portion 52a which extends from a proximal end of loading unit 40 which engages the opposing articulation link 57 coupled to the actuation assembly 35a of the adapter assembly 30. Articulation link 52 has a distal end portion 52b pivotably secured to end effector 44. As the articulation link 57 is moved in an axial direction by the actuation assembly 35a of the adapter assembly 30, either proximally or distally, the articulation link 52 of the loading unit 40 is also moved in the same manner. Axial movement of the articulation link 52, in turn, articulates (e.g., pivots) the end effector 44 about a pivot pin 59, which defines the axis Y-Y.

Figure 8:
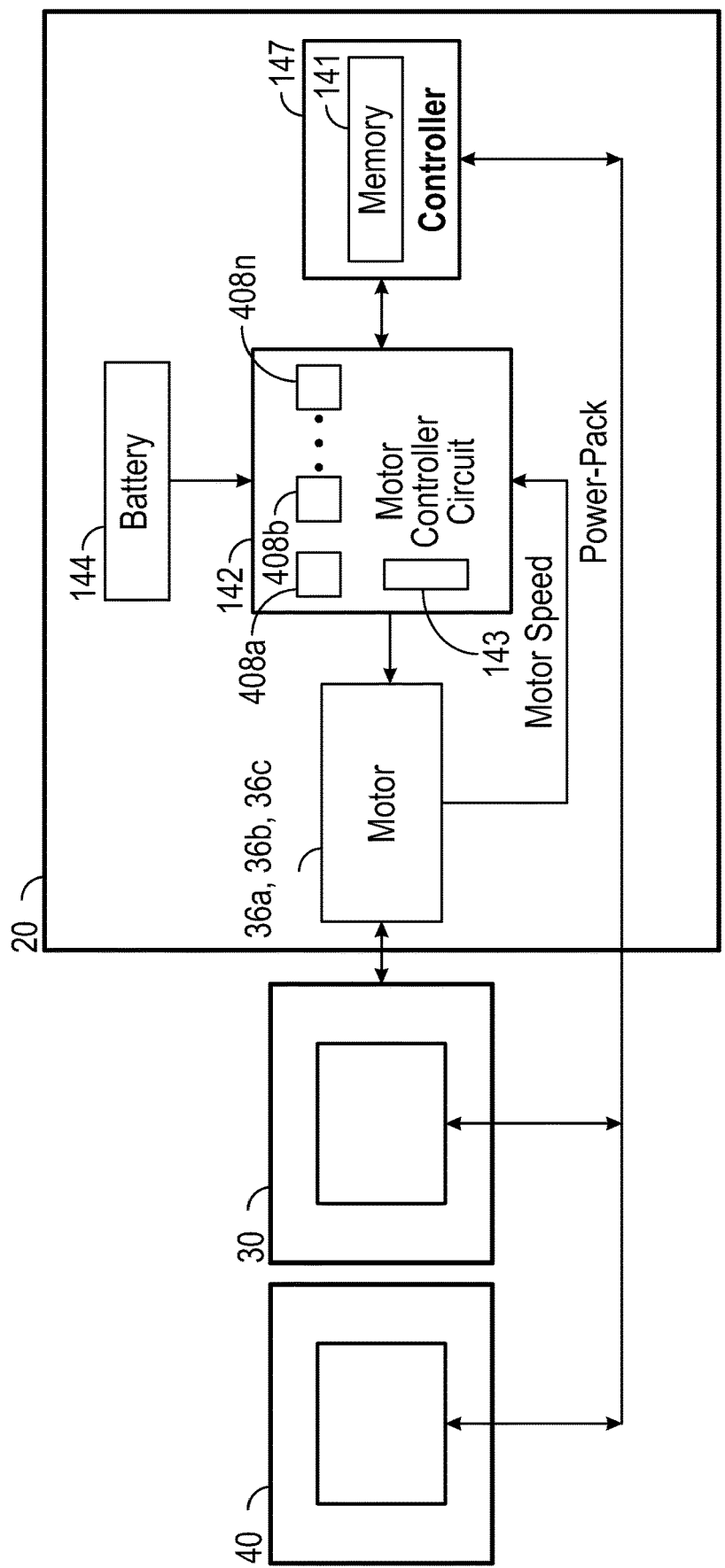
FIG. 8 is a schematic diagram of the handle assembly, the adapter assembly, and the end effector of FIG. 1.

With reference to FIG. 8, the handle assembly 20 includes the main controller circuit board 142, the rechargeable battery 144 configured to supply power to any of the electrical components of handle assembly 100, and a plurality of motors 36a, 36b, 36c coupled to the battery 144. The handle assembly 20 also includes the display 146. In embodiments, the motors 36a, 36b, 36c may be coupled to any suitable power source configured to provide electrical energy to the motors 36a, 36b, 36c, such as an AC/DC transformer. Each of the motors 36a, 36b, 36c is coupled a motor controller 143 which controls the operation the motors 36a, 36b, 36c, including the flow of electrical energy from the battery 144 to the motors 36a, 36b, 36c. A main controller 147 is provided that controls the handle assembly 20. The main controller 147 is configured to execute software instructions embodying algorithms disclosed herein, such as clamping, stapling, and cutting algorithms which control operation of the handle assembly 20.

The motor controller 143 includes a plurality of sensors 408 (e.g., 408a . . . 408n) configured to measure operational states of the motors 36a, 36b, 36c and the battery 144. The sensors 408 include a strain gauge 408b and may also include voltage sensors, current sensors, temperature sensors, telemetry sensors, optical sensors, and combinations thereof. The sensors 408 may measure voltage, current, and other electrical properties of the electrical energy supplied by the battery 144. One of the sensors 408, namely, a sensor 408a may measure angular velocity (e.g., rotational speed) as revolutions per minute (RPM), torque, temperature, current draw, and other operational properties of the motor 36a. The sensor 408a may also include an encoder configured to count revolutions or other indicators of the motor 36a, which is then use by the main controller 147 to calculate linear movement of components movable by the motor 36a. Angular velocity may be determined by measuring the rotation of the motors 36a, 36b, 36c or a drive shaft (not shown) coupled thereto and rotatable by the motors 36a, 36b, 36c. The position of various axially movable drive shafts may also be determined by using various linear sensors disposed in or in proximity to the shafts or extrapolated from the RPM measurements. In embodiments, torque may be calculated based on the regulated current draw of the motors 36a, 36b, 36c at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motor 36a.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 36a, 36b, 36c and the battery 144 and, in turn, outputs control signals to the motor controller 143 to control the operation of the motors 36a, 36b, 36c based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the handle assembly 20. The main controller 147 is also coupled to the strain gauge 408b of the adapter assembly 200 using a wired or a wireless connection and is configured to receive strain measurements from the strain gauge 408b which are used during operation of the handle assembly 20.

The handle assembly 20 includes a plurality of motors 36a, 36b, 36c each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100.

Figure 9:
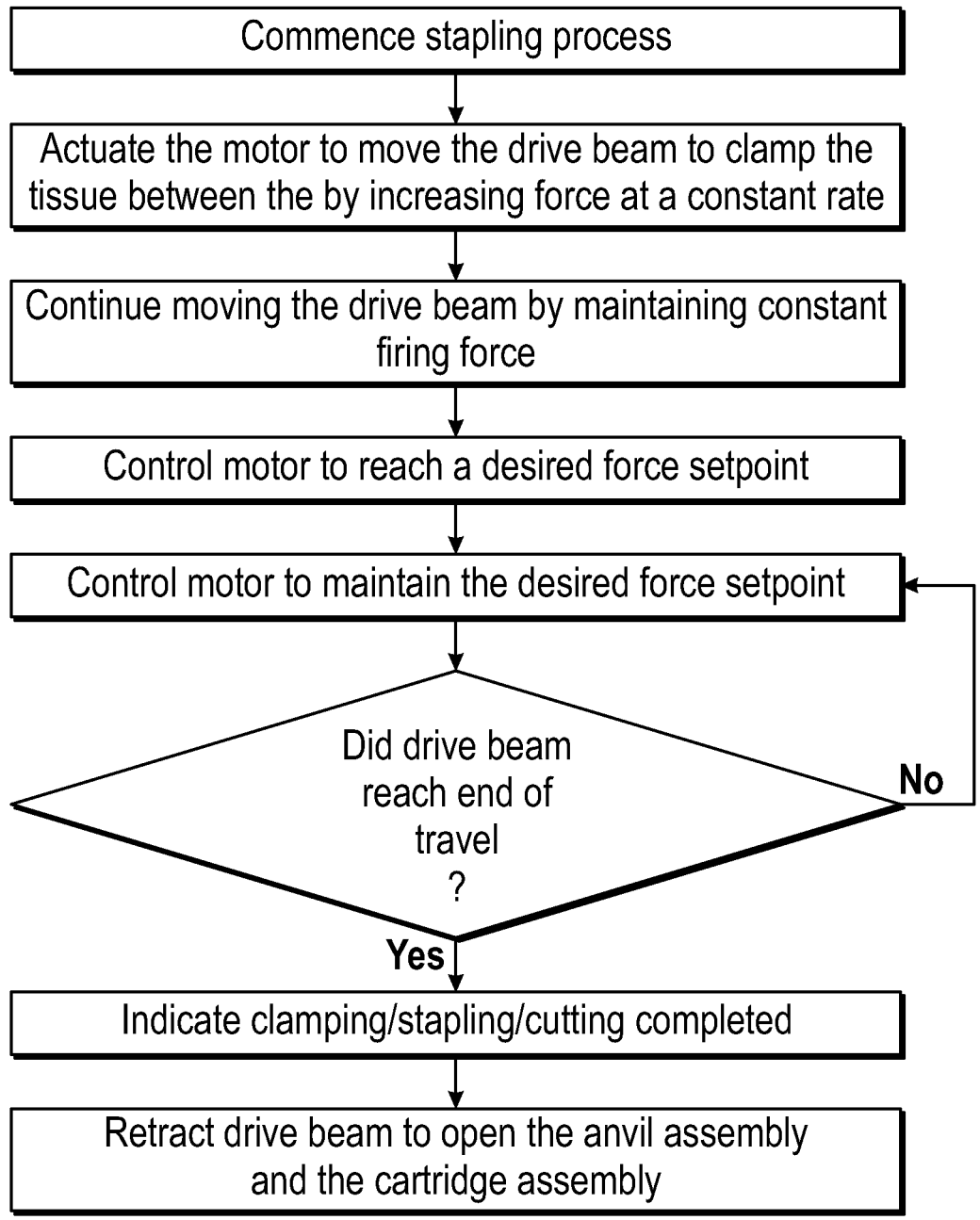
FIG. 9 is flow chart of a control algorithm controlling the surgical instrument of FIG. 1 according to an embodiment of the present disclosure.

A method for actuating the end effector 44 to clamp, staple, and cut the tissue is shown in FIG. 9. The process is commenced by positioning the tissue between the anvil assembly 46 and the cartridge assembly 48 and pressing one of the buttons 27. The main controller 147 receives the input from one of the buttons 27 and instructs the motor controller 143 to output a control signal to the motor 36b responsible for actuating the end effector 44. The motor controller 143 is configured to output a pulse-width modulated (PWM) control signal, which allows to adjust the power supplied to the motor 36b in discrete increments. The motor controller 143 may include a proportional-integral-derivative (PID) controller or any other suitable control loop circuit using feedback signals to achieve a desired setpoint. The parameters of the PID loop or control loop can be configurable based on various inputs, data collected during clamp, reload type, tissue type e.g., sensing tissue type or manually entering tissue type.

Figure 10:
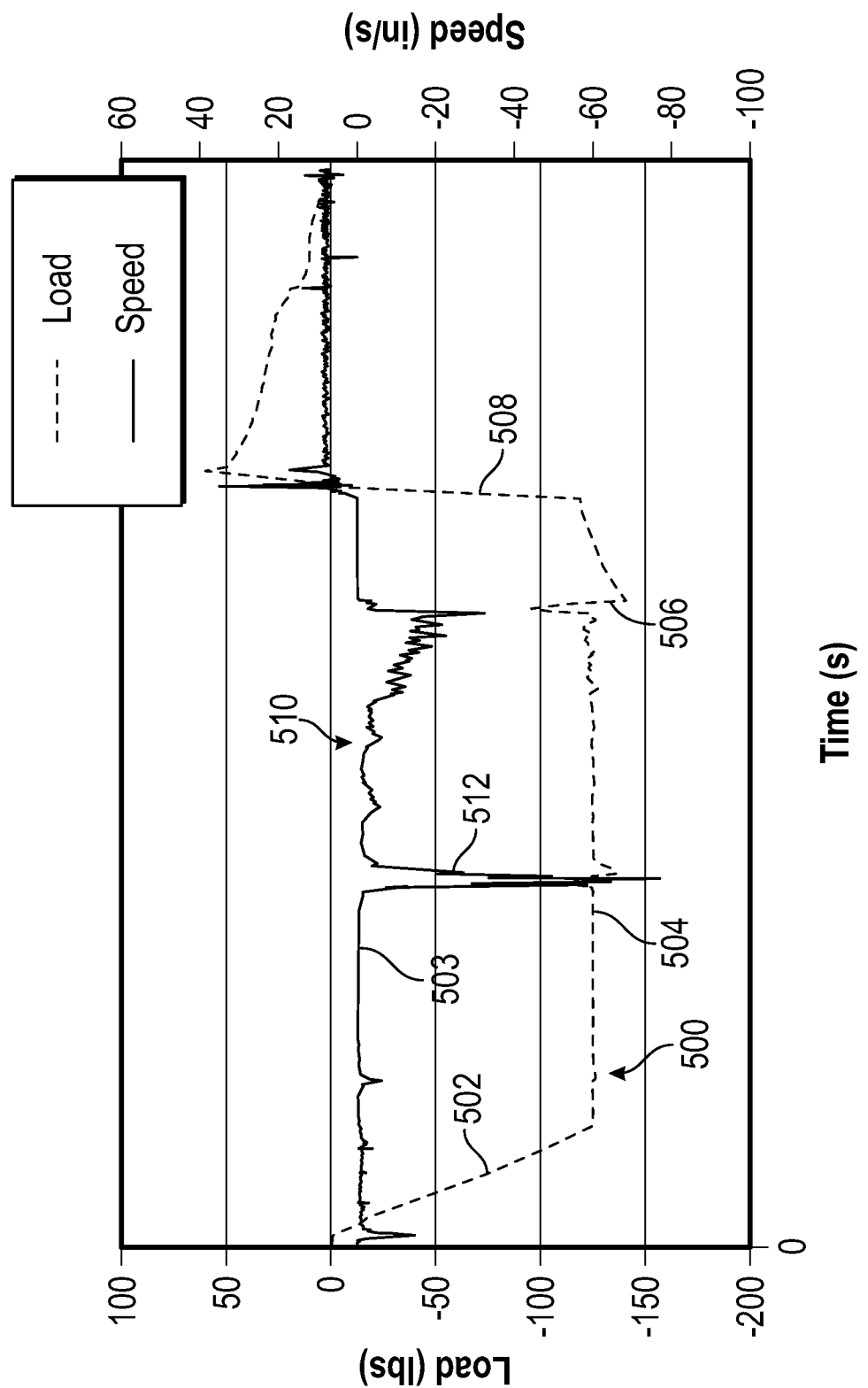
FIG. 10 shows plots of a load imparted on a drive beam and the rotation speed of the motor during the control algorithm of FIG. 9 according to an embodiment of the present disclosure.

The motor controller 143 controls the motor 36b to move the drive beam 54 in a distal direction to commence clamping. In response, the drive beam 54 closes the anvil assembly 46 and the cartridge assembly 48 and simultaneously advances the knife 55a and the actuation sled 66. As a result of actuation of these components a force is imparted on the drive beam 54. FIG. 10 which shows superimposed plots 500 and 510, with the plot 500 showing the load imparted on the drive beam 54 as measured by the strain gauge 408b and the plot 510 illustrating the rotation speed of the motor 36b and/or linear speed of the drive beam 54, respectively.

Initially, the motor controller 143 adjusts the motor 36b to ramp the force at a constant rate as shown in a segment 502 of the force plot 500 until a setpoint force is reached. Once the setpoint is reached, the force is maintained during a segment 504. The speed of the motor 36b may vary during the constant force segment 504 as shown by a spike 512 in the speed plot 510, while the constant force is maintained. In embodiments, the linear speed of the drive beam 54 and/or the rotation speed of the motor 36b may also be held constant during a segment 503, at least until the spike 512 is reached, which is contemporaneous with the constant force segment 504. The drive beam 54 is advanced while the constant force is maintained during the segment 504 until the drive beam 54 reaches an end of travel position, which corresponds to the knife 55a and/or the anvil assembly 46.

End of travel may be determined using the sensor 408a, which determines position of the drive beam 54 based on the revolutions of the motor 36b or any other suitable position sensor. In embodiments, end of travel may be determined using the strain gauge 408b which can detect a mechanical stop encountered by the drive beam 54. Once end of travel is determined, the motor 36b stops advancing the drive beam 54 and withdraws the drive beam 54 to open the anvil assembly 46 and the cartridge assembly 48. End of travel and withdrawal of the drive beam 54 is indicated by a spike 506 and a segment 508, respectively. More specifically, the spike 506 indicates reaching the mechanical limit and the segment 508 indicates reversal of the drive beam 54.

It is envisioned that the constant force algorithm according to the present disclosure may be used with any jaw type powered or robotic surgical instrument as well as end-to-end anastomosis circular staplers, and the like. It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a pair of opposing jaw members, wherein one jaw member of the pair of opposing jaw members includes a plurality of staples and a longitudinal slot;
   an actuation sled movable through the one jaw member of the pair of opposing jaw members to eject the plurality of staples;
   a drive beam movable longitudinally through the pair of opposing jaw members from a proximal-most position of the longitudinal slot to a distal-most end of the longitudinal slot, thereby approximating the pair of opposing jaw members relative to each other and moving the actuation sled through the one jaw member of the pair of opposing jaw members;
   a motor configured to move the drive beam;
   a sensor configured to measure a force imparted on the drive beam; and
   a motor controller configured to control the motor to maintain constant force on the drive beam during approximation of the pair of opposing jaw members relative to each other and ejection of the plurality of staples, wherein constant force is maintained based on the force measured by the sensor during longitudinal movement of the drive beam until the drive beam reaches the distal-most end of the longitudinal slot.

2. The surgical device according to claim 1, wherein the drive beam further includes a distally facing knife.

3. The surgical device according to claim 1, wherein the motor controller includes a proportional-integral-derivative (PID) controller configured to receive the measured force as input and to output motor control signals to maintain the constant force on the drive beam.

4. The surgical device according to claim 3, wherein the motor control signals are pulse-width-modulated.

5. The surgical device according to claim 3, wherein the motor controller is further configured to ramp up to the constant force at a constant rate.

6. The surgical device according to claim 1, further comprising:
   a handle assembly including:
      a user input button; and
      a main controller configured to receive an input signal from the user input button and to signal the motor controller to control the motor.

7. A surgical device comprising:
   an end effector including:
      an anvil assembly;
      a cartridge assembly having a plurality of staples and a longitudinal slot; and
      a drive beam movable longitudinally through the anvil assembly and the cartridge assembly thereby approximating the anvil assembly and the cartridge assembly from a proximal-most position of the longitudinal slot to a distal-most end of the longitudinal slot relative to each other and ejecting the plurality of staples;

an adapter assembly configured to selectively couple to the end effector, the adapter assembly including an actuation assembly configured to mechanically engage the drive beam and to move the drive beam longitudinally; and a handle assembly configured to selectively couple to the adapter assembly, the handle assembly including:
- a power source;
- a motor coupled to the power source;
- a sensor configured to measure a force imparted on the drive beam; and
- a motor controller configured to control the motor to maintain constant force on the drive beam during approximation of the anvil assembly and the cartridge assembly relative to each other and ejection of the plurality of staples, wherein constant force is maintained based on the force measured by the sensor during longitudinal movement of the drive beam until the drive beam reaches the distal-most end of the longitudinal slot.

8. The surgical device according to claim 7, wherein the end effector further includes an actuation sled movable through the cartridge assembly and configured to eject the plurality of staples.

9. The surgical device according to claim 8, wherein the drive beam is configured to engage the actuation sled to move the actuation sled through the cartridge assembly.

10. The surgical device according to claim 7, wherein the drive beam further includes a distally facing knife.

11. The surgical device according to claim 7, wherein the motor controller includes a proportional-integral-derivative (PID) controller configured to receive the measured force as input and to output motor control signals to maintain the constant force on the drive beam.

12. The surgical device according to claim 11, wherein the motor control signals are pulse-width-modulated.

13. The surgical device according to claim 11, wherein the motor controller is configured to ramp up to the constant force at a constant rate.

14. A method for controlling a surgical device, the method comprising:
- activating a motor coupled to a drive beam configured to move longitudinally through an anvil assembly and a longitudinal slot of a cartridge assembly of an end effector from a proximal-most position of the longitudinal slot to a distal-most end of the longitudinal slot;
- approximating the anvil assembly and the cartridge assembly relative to each other;
- ejecting a plurality of staples disposed in the cartridge assembly;
- measuring force imparted on the drive beam; and
- controlling the force imparted on the drive beam to remain constant at a setpoint during longitudinal movement of the drive beam while the anvil assembly and the cartridge assembly are approximated relative to each other and the plurality of staples are ejected, wherein constant force is maintained based on the force measured during longitudinal movement of the drive beam until the drive beam reaches the distal-most end of the longitudinal slot.

15. The method according to claim 14, further comprising ramping up the force imparted on the drive beam at a constant rate to reach the setpoint.

16. The method according to claim 14, further comprising:
- advancing a knife through the anvil assembly and the cartridge assembly.

17. The method according to claim 14, wherein controlling the force further includes:
- processing the measured force as input at a proportional-integral-derivative (PID) controller; and
- outputting motor control signals from the PID controller to maintain the constant force on the drive beam.

\* \* \* \* \*